United States Patent [19]

Dunbar et al.

[11] 4,343,647
[45] Aug. 10, 1982

[54] SUBSTITUTED BENZYLTRIALKYLAMMONIUM SALTS AND THEIR USE AS PLANT GROWTH REGULATORY CONTROL AGENTS

[75] Inventors: Joseph Dunbar, Midland, Mich.; Theodore W. Holmsen, Clayton, Calif.; Herman O. Senkbeil, Midland, Mich.

[73] Assignee: The Dow Chemical Company, Midland, Mich.

[21] Appl. No.: 157,755

[22] Filed: Jun. 9, 1980

Related U.S. Application Data

[63] Continuation of Ser. No. 11,746, Feb. 13, 1979, abandoned, which is a continuation-in-part of Ser. No. 950,202, Oct. 10, 1978, abandoned, which is a continuation-in-part of Ser. No. 742,170, Nov. 15, 1976, abandoned.

[51] Int. Cl.$^3$ .............. A01N 33/04; C07C 87/30
[52] U.S. Cl. .......................... 71/76; 71/121; 564/288; 564/289
[58] Field of Search ............ 260/567.6 F, 567.6 H, 260/567.6 M; 71/121, 76; 564/288, 289, 282

[56] References Cited

U.S. PATENT DOCUMENTS

| | | |
|---|---|---|
| 2,689,789 | 9/1954 | Mowry et al. .......................... 71/121 |
| 3,037,910 | 6/1962 | Copp et al. ............. 260/567.6 M X |
| 3,156,554 | 11/1964 | Tolbert .................................. 71/121 |
| 3,218,356 | 11/1965 | Melton ......................... 260/567.6 M |
| 3,280,137 | 10/1966 | Wakeman et al. ...... 260/567.6 M X |
| 3,671,219 | 6/1972 | Nickell ................................... 71/121 |
| 3,850,611 | 11/1974 | Nakanish et al. .................. 71/76 X |

FOREIGN PATENT DOCUMENTS 924146  6/1960  United Kingdom .

OTHER PUBLICATIONS

Moshin et al. Chem. Abst. vol. 77 (1972) 136164d.
Knight et al. Chem. Abst. vol. 71 (1969), 21086p.

*Primary Examiner*—Catherine L. Mills
*Attorney, Agent, or Firm*—Ronald G. Brookens; S. Preston Jones

[57] ABSTRACT

Compounds are prepared which correspond to the formula

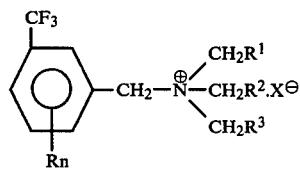

wherein R represents hydrogen, chloro, bromo or trifluoromethyl; n represents an integer of from 1 or 2 with the proviso that when R is trifluoromethyl, n is 1; $R^1$, $R^2$ and $R^3$ each independently represent ethyl, n-propyl, n-butyl, isobutyl, ethynyl, vinyl or ethoxymethyl or $R^2$ and $R^3$ taken together form an alkylene bridge of 2 to 4 carbon atoms and X represents a non-phytotoxic anion. The compounds have been found to be active plant growth regulatory control agents.

46 Claims, No Drawings

SUBSTITUTED BENZYLTRIALKYLAMMONIUM SALTS AND THEIR USE AS PLANT GROWTH REGULATORY CONTROL AGENTS

CROSS-REFERENCE TO RELATED APPLICATION

This is a continuation of application Ser. No. 011,746 filed Feb. 13, 1979, abandoned, which is a continuation-in-part of Application Ser. No. 950,202, filed Oct. 10, 1978, which in turn is a continuation-in-part of Application Ser. No. 742,170, filed Nov. 15, 1976, both now abandoned.

BACKGROUND OF THE INVENTION

One active area of agricultural research is devoted to the production of more productive plant life, particularly that plant life usually considered as or associated with food sources or beauty for man. In this research, much effort has been expended in developing means for the regulation of the growth pattern of plant life, particularly as evidenced by the retardation of growth and the enhancement of maturation.

These objectives have been accomplished, in part, by the discovery, development and distribution of various chemical agents which alter or modify the growth characteristics of plants. Documentation of such can be found in Dwarfing Plants With Chemicals, Agricultural Research Service, U.S. Dept. of Agriculture, January, 1961.

PRIOR ART

Various ammonium salts have been employed in the control of plant growth. For example, diethylmethyl-(2-phenylalkyl)ammonium iodide is taught in U.S. Pat. No. 3,539,632. The compounds, tetraisopentylammonium bromide and its corresponding chloride are taught in U.S. Pat. No. 3,580,716. Related (loweralkyl carboxy benzyl) trialkylammonium compounds are taught in U.S. Pat. No. 3,923,495. Tributyl-2,4-dichlorobenzylammonium chloride is taught in U.S. Pat. No. 3,218,356. Various tetraalkylammonium salts are further taught in U.S. Pat. No. 2,740,744. Substituted benzyl trialkyl ammonium halides are taught in U.S. Pat. No. 2,772,310. Various quaternary ammonium florides are taught in U.S. Pat. No. 3,277,118. Additional plant growth regulators such as di- and trimethyl(cycloalkyl or alkenyl)ammonium salts are found in U.S. Pat. No. 3,884,670 and the closely related n-alkylbenzalkonion halide compounds as found in German Pat. No. 2,415,981 (abstract found in Derwent (Agdoc) page 11, Week W42).

SUMMARY OF THE INVENTION

The present invention is directed to compounds corresponding to the general formula

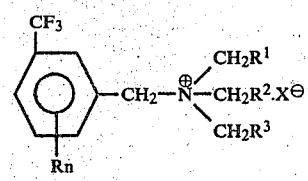

wherein R represents hydrogen, chloro, bromo or trifluoromethyl; n represents an integer of from 1 or 2, with the proviso that when R is trifluoromethyl, n is 1; $R^1$, $R^2$ and $R^3$ each independently represent ethyl, n-propyl, n-butyl, isobutyl, ethynyl, vinyl or ethoxyethyl or $R^2$ and $R^3$ taken together form an alkylene bridge of 2 to 4 carbon atoms and X represents a non-phytotoxic anion.

The compounds of the above formula have been found to be active in causing a reduction (i.e., stunting) of the linear growth of various plants. The compounds are particularly effective in altering the growth pattern of many plants such as food crops, ornamental plants and especially trees. The treated plants exhibit a compact growth habit, reduced water uptake and a darker leaf coloration.

One of the typical effects of plant growth control agents is a reduction or decrease in plant height. Similarly, seed germination can be stimulated and flowering can be induced. It is therefore possible to employ plant growth control agents to influence the plants' natural growth rhythm.

An additional effect observed from the action of the compounds of the present application lies in the reduced water uptake of many plant species treated with the compounds. This effect is very pronounced at levels of the specific compound which may not inhibit the growth of the plant. The effect of this reduced water uptake of the plants is that treated plants can thrive under conditions of reduced available soil moisture where untreated plants may not survive.

The substituted benzyltrialkylammonium salts of the present invention are crystalline solids or oils, soluble in water and appreciably soluble in common organic solvents.

The specific anion of the salts of the present invention is not critical. The anion can be any of the anions conventionally employed in plant growth regulators. The only limitation upon the anion chosen is that it be non-phytotoxic to the plants being treated. Representative anion include $Cl^{(-)}$, $Br^{(-)}$, $I^{(-)}$, $SCN^{(-)}$, $CH_3CO_2^{(-)}$, $C_2H_5CO_2^{(-)}$, $\phi SO_3^{(-)}$, $\phi CO_2^{(-)}$, $Cl\text{-}\phi\text{-}O^{(-)}$, $C_3H_7CO_2^{(-)}$, $SO_4^{(=)}$, $PO_4^{(\equiv)}$, $NO_3^{(-)}$, $ClO_3^{(-)}$, and $N_3^{(-)}$, among others.

The compounds of the present invention can be prepared by the reaction of an appropriate substituted (trifluoromethyl)benzylhalide (usually a chloride or bromide) and an appropriate trialkylsubstituted amine in the presence of a solvent.

The reaction can be characterized as follows:

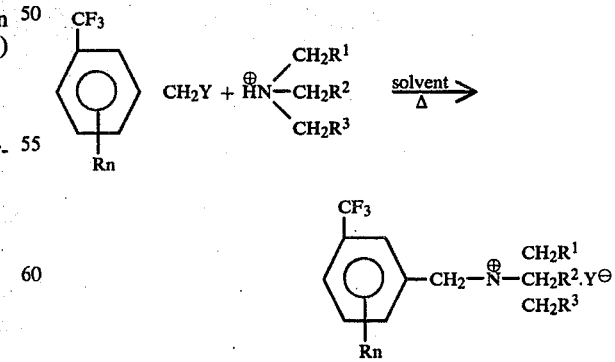

wherein R, N, $R^1$, $R^2$ and $R^3$ are as hereinbefore defined and Y is chlorine or bromine.

In carrying out this reaction, the reactants and solvent are mixed together in any suitable fashion and the mixture heated at a temperature in the range of from about 65° to about 150° C. (dependent upon the reactants) and preferably at the reflux temperature of the mixture. The reactants are maintained under such conditions until the reaction is complete. Since the reaction is rather slow, reaction period of from about 2 hours to 1 week or more are not unusual. The specific time period is dependent upon the specific reactants and solvents employed.

The amount of the reactants to be employed is not critical, some of the product being formed when employing any proportions. The reaction, however, consumes the reactants in the ratio of one mole of the benzyl halide per mole of the amine and the employment of such proportions is preferred.

It is preferred to employ polar solvents in carrying out this reaction. Representative solvents include, for example, acetonitrile, butanol, nitromethane and methyl ethyl ketone. When lower boiling solvents are employed, pressures higher than atmospheric may be necessary to permit the use of temperatures higher than the boiling point of the solvent. It is also within the scope of this invention to conduct the reaction in the absence of solvents provided that adequate control is maintained over the temperature.

Upon completion of the reaction, the product is removed from the reaction mixture. This separation can be achieved by (a) removing the solvent by evaporation under reduced pressure and recovering the product as a residue or (b) cooling the reaction mixture and mixing it with a solvent such as, for example, ethyl ether, hexane or mixtures thereof. If the product is solid, it can be separated by filtration or other known solid-liquid separation techniques; if the product is a liquid (oil), it can be separated by decantation or other conventional separation techniques. If desired, solid products can be further purified by recrystallization from solvents such as, for example, methyl ethyl ketone, ethyl acetate, ethyl ether, hexane, ethanol or mixtures thereof. The liquid products can sometimes be crystallized by trituration with the appropriate solvent.

While the above preparative procedures have been described wherein the product is in the form of the chloride or bromide salt (the benzylchloride or bromide having been the starting reactant), other salts can be prepared employing conventional procedures.

Such additional salts are prepared by treating the chloride or bromide product at room temperature in water with the alkali or alkaline earth salt of the organic or inorganic acid from which the desired anion is derived. This salt is of the formula

M⊕X⊖ wherein M represents the alkali metals such as sodium, potassium, lithium, cesium or rubidium and the alkaline earth metals such as calcium, barium or strontium and X is as hereinabove set forth. These additional salts can also be prepared by passing the product bromide or chloride salt through an ion exchange column charged with the appropriate anion.

DESCRIPTION OF SOME PREFERRED EMBODIMENTS

The following examples illustrate the present invention and the manner by which it can be practical but, as such, should not be construed as limitations upon the overall scope of the same.

EXAMPLE I

Triisopentyl (3-(trifluoromethyl)benzyl) ammonium chloride

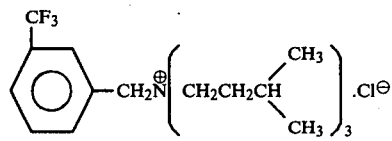

A mixture of 38.8 grams (0.200 mole) of 3-(trifluoromethyl)benzylchloride and 45.4 grams (0.200 mole) of triisopentylamine in 75 milliliters of acetonitrile was heated under reflux for 96 hours. At the end of this time period, the reaction mixture was cooled to room temperature and poured into 1800 milliliters of ethyl ether. The solution was cooled in an ice bath and the crystals which precipitated were collected by filtration and dried. The remaining ether solution was concentrated and cooled to give additional solid crude product which was recovered by filtration, dried and combined with the first crop. The crude product was recrystallized from a mixture of ethyl acetate and ethyl ether. The crude triisopentyl (3-(trifluoromethyl)benzyl) ammonium chloride was recovered in a yield of 44 grams (52 percent of theoretical) and melted at 121°–127° C. Upon analysis, the product was found to have carbon, hydrogen and nitrogen contents of 65.00, 9.33 and 3.63 percent, respectively, as compared to the theoretical contents of 65.46, 9.32 and 3.32 percent respectively, calculated for the above named product. The structure of the compound was confirmed by nuclear magnetic resonance spectroscopy (NMR) (Compound 1).

EXAMPLE II

Tri-n-butyl (3-(trifluoromethyl)benzyl) ammonium chloride

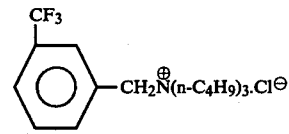

A mixture of 36.2 grams (0.186 mole) of 3-(trifluoromethyl)benzyl chloride and 34.4 grams (0.186 mole) of tri-n-butyl amine in 50 milliliters of acetonitrile was heated under reflux for ∼120 hours. At the end of this period, the reaction mixture was cooled and poured into ∼500 milliliters of ethyl ether. The crude product which precipitated was recovered by filtration and dried. The crude product was mixed with 600 milliliters of hot methyl ethyl ketone and filtered and then mixed with 1 liter of hexane. The tri-n-butyl (3-trifluoromethyl)benzyl) ammonium chloride precipitated and was recovered by filtration in a yield of 42 grams (59.5 percent of theoretical). The product melted at 171°–172° C. The structure of the compound was confirmed by NMR (Compound 2).

EXAMPLE III

Tri-n-pentyl (3-(trifluoromethyl)benzyl) ammonium chloride

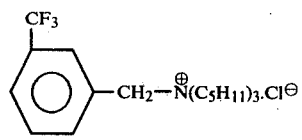

A mixture of 17.8 grams (0.092 mole) of 3-(trifluoromethyl)benzylchloride and 20.8 grams (0.092 mole) of tri-n-pentylamine in 50 milliliters of acetonitrile was heated overnight (~16 hours) at 90°-95° C. At the end of this period, the reaction mixture was cooled and poured into ~500 milliliters of ethyl ether. The crude product was recovered by vacuum filtration. The crude tri-n-pentyl (3-(trifluoromethyl)benzyl)ammonium chloride product was recrystallized from a methyl ethyl ketone-hexane mixture and dried. The product was recovered in a yield of 27.6 grams (71.5 percent of theoretical) and melted at 151.5°-152.5° C. The structure of the compound was confirmed by NMR (Compound 3).

EXAMPLE IV

Tri-n-propyl (3-(trifluoromethyl)benzyl)ammonium chloride

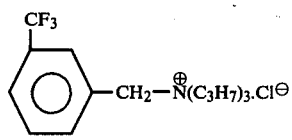

A mixture of 19.45 grams (0.1 mole) of 3-(trifluoromethyl)benzyl chloride and 14.30 grams (0.1 mole) of tri-n-propylamine in 25 milliliters of acetonitrile was heated overnight (~16 hours), with stirring in an oil bath at 95° C. The reaction mixture was cooled and poured into ~500 milliliters of ethyl ether. The solid which precipitated was recovered by vacuum filtration. The crude material was dissolved in ~350 milliliters of hot methyl ethyl ketone and filtered to remove insoluble materials. The ketone solution was allowed to slowly cool to room temperature and the solid tri-n-propyl (3-(trifluoromethyl)benzyl)ammonium chloride product which precipitated was recovered by vacuum filtration and thoroughly dried. The product was recovered in a yield of 19.56 grams melting at 173°-174° (dec). The structure of the compound was confirmed by NMR (Compound 4).

EXAMPLE V

Tri-n-butyl(2-chloro-5-(trifluoromethyl)benzyl)ammonium chloride

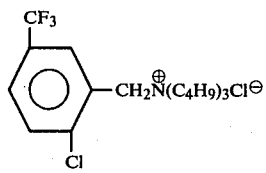

A mixture of 16.8 grams (0.073 mole) of 2-chloro-5-(trifluoromethyl)benzylchloride and 13.6 grams (0.073 mole) of tri-n-butyl amine in 50 milliliters of acetonitrile was heated and stirred overnight at a temperature of 90°±5° C. At the end of this period, the reaction mixture was cooled and the acetonitrile was removed by evaporation under reduced pressure. The residue which remained was mixed with ethyl ether and the solid precipitate which formed was removed by vacuum filtration. This crude product was dissolved in 100 milliliters of hot methyl ethyl ketone, filtered to remove insolubles. To this solution was added 50 milliliters of hexane and the tri-n-butyl(2-chloro-5-(trifluoromethyl)benzyl)ammonium chloride product which precipitated was recovered by filtration and dried. The product was recovered in a yield of 14.4 grams and melted at 116°-117.5° C. The structure of the compound was confirmed by NMR (Compound 5).

EXAMPLE VI

N,N-di-n-butyl-N-propargyl (3-(trifluoromethyl)benzyl)ammonium bromide

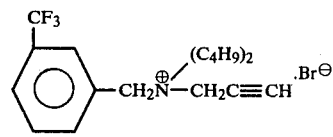

A mixture of 14.35 grams (0.05 mole) of di-n-butyl-3-(trifluoromethyl)benzyl amine and 6.00 grams (0.05 mole) of propargyl bromide in 25 milliliters of acetonitrile. The mixture was heated at 80° C., with stirring for about 8 hours and thereafter for about 64 hours at room temperature. The temperature was raised to 90°-95° C. and the mixture was heated at this temperature, with stirring, for ~24 hours. The solvent was thereafter removed by evaporation under reduced pressure and the viscous residue which remained was extracted with ethyl ether followed by crystallization from a mixture of methyl ethyl ketone and hexane. The solvents were removed by evaporation under reduced pressure and the N,N-dibutyl-N-propargyl (3-(trifluoromethyl)benzyl)ammonium bromide product was recovered in a yield of 15.7 grams. The product melted at 93°-97° C. The structure of the compound was confirmed by NMR (Compound 6).

EXAMPLE VII

Tri-n-butyl (3-trifluoromethyl)benzyl)ammonium iodide

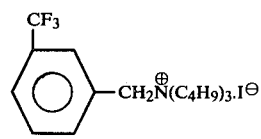

To a solution of 5.7 grams (0.015 mole) of tri-n-butyl (3-(trifluoromethyl)benzyl)ammonium chloride dissolved in 20 milliliters of water was added a solution of 2.5 grams (0.015 mole) of potassium iodide dissolved in 10 milliliters of water. A white, opaque material precipitated immediately. This material was triturated with ether and the solid which formed was removed by vacuum filtration. The crude product was obtained in a yield of 7.3 grams and melted at 80°-100° C. The tri-n-butyl (3-(trifluoromethyl)benzyl)ammonium iodide was purified by crystallization from a 1:1 mixture of methyl ethyl ketone and was recovered in a yield of 73.6 percent of theoretical and melted at 125°-128° C. The structure of the product was confirmed by NMR (Compound 7).

EXAMPLE VIII

Tri-n-butyl (3-(trifluoromethyl)benzyl)ammonium azide

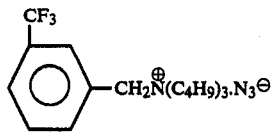

To a solution of 11.4 grams (0.030 mole) of tri-n-butyl (3-(trifluoromethyl)benzyl)ammonium chloride dissolved in 25 milliliters of water was added a solution of 6.5 grams (0.10 mole) of sodium azide in 25 milliliters of water. An oil and water layer formed. The water layer was decanted off and the oil layer was taken up in methylene chloride, dried and vacuum filtered. The methylene chloride was removed by evaporation under reduced pressure and the residual oil was crystallized by trituration with ether, vacuum filtered and air dried. The tri-n-butyl (3-(trifluoromethyl)benzyl)ammonium azide product was recovered in a yield of 6.9 grams (59.6 percent of theoretical) and melted at 67°–70° C. The structure of the product was confirmed by NMR (Compound 8).

EXAMPLE IX

Tri-n-butyl(3-(trifluoromethyl)benzyl)ammonium chlorate

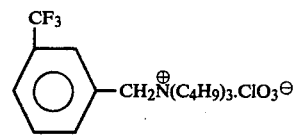

A solution of 11.4 grams (0.030 mole) of tri-n-butyl(3-(trifluoromethyl)benzyl)ammonium chloride dissolved in 50 milliliters of water was added to a solution of 6.4 grams (0.060 mole) of sodium chlorate in 50 milliliters of water. A viscous material precipitated. The water layer was decanted off and the viscous material was dissolved in methylene chloride, dried and vacuum filtered. The methylene chloride was removed by evaporation under reduced pressure to obtain 12.2 grams of the crude tri-n-butyl(3-trifluoromethyl)benzyl)ammonium chlorate as a liquid residue. The crude material was triturated with ether and the white precipitate which formed was recovered by vacuum filtration. The product was recovered in a yield of 9.3 grams (72.5 percent of theoretical) and melted at 87°–91° C. The structure of the product was confirmed by NMR (Compound 9).

By following the preparative procedures as set forth in the above examples and employing the appropriate starting reactants, the following compounds are prepared.

TABLE I

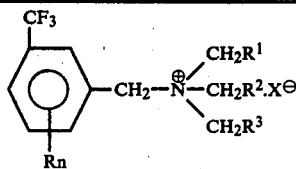

| Compound No. | R | $R^1$ | $R^2$ | $R^3$ | $X^-$ | M.P. °C. | Ref. Index $n^{25}/d$ | Mol. Wt. |
|---|---|---|---|---|---|---|---|---|
| 10 | H | —$C_3H_7$ | —$C_3H_7$ | —CH=$CH_2$ | Br | — | 1.5160 | 408.0 |
| 11 | H | —CH=$CH_2$ | —CH=$CH_2$ | —CH=$CH_2$ | Cl | 118–121 | — | 331.5 |
| 12 | 4,6-$Cl_2$ | —$C_3H_7$ | —$C_3H_7$ | —$C_3H_7$ | Cl | 135–137 | — | 448.5 |
| 13 | 4-Cl | —$C_3H_7$ | —$C_3H_7$ | —$C_3H_7$ | Cl | 179–180.5 | — | 414.0 |
| 14 | H | —$C_3H_7$ | —$C_3H_7$ | —$C_3H_7$ | $\phi SO_3$ | — | — | 501.7 |
| 15 | H | —$C_3H_7$ | —$C_3H_7$ | —$C_3H_7$ | Br | 170–172 | — | 424.0 |
| 16 | H | —$C_3H_7$ | —$CH_2OC_2H_5$ | —$CH_2OC_2H_5$ | Br | 102–105 | — | 456.0 |
| 17 | H | —$C_2H_5$ | —$C_3H_7$ | —$C_3H_7$ | Cl | 172–173.5 | — | 365.5 |
| 18 | H | —$C_3H_7$ | —$C_3H_7$ | —$C_3H_7$ | $NO_3$ | 90–92 | — | 406.0 |
| 19 | 6-Br | —$C_2H_5$ | —$C_2H_5$ | —$C_2H_5$ | $SO_4$ | — | — | 413.4 |
| 20 | H | —$C_3H_7$ | —$C_3H_7$ | —$C_3H_7$ | $CH_3CO_2$ | — | 1.4650 | 403.0 |
| 21 | H | —$C_3H_7$ | —$C_3H_7$ | —$C_3H_7$ | $C_3H_7CO_2$ | — | 1.4655 | 431.0 |
| 22 | 5-$CF_3$ | —i-$C_4H_9$ | —($CH_2$)$_4$— | | $\phi CO_2$ | — | — | 421.5 |
| 23 | 5-$CF_3$ | —i-$C_4H_9$ | —($CH_2$)$_2$— | | Cl | — | — | 421.5 |
| 24 | 5-$CF_3$ | —$C_3H_7$ | —$C_3H_7$ | —$C_3H_7$ | Cl | 170–172 | — | 391.2 |
| 25 | H | —$C_3H_7$ | —$C_3H_7$ | —$C_3H_7$ | Cl | 143–146 | — | 323.8 |
| 26 | H | —$C_3H_7$ | —$C_3H_7$ | —$C_3H_7$ | SCN | 77–80 | — | 402.0 |
| 27 | H | —$C_3H_7$ | —$C_3H_7$ | —$C_3H_7$ | 3-Cl$\phi$—O— | — | 1.5385 | 471.5 |
| 28 | H | —$C_3H_7$ | —$C_3H_7$ | —$C_3H_7$ | $\phi SO_3$ | — | 1.5090 | 501.0 |
| 29 | H | —$C_3H_7$ | —$C_3H_7$ | —$C_3H_7$ | $C_2H_5CO_2$ | 143–145 | — | 465.5 |

It has been discovered that the compounds of the present invention can be employed as plant growth control agents. In this capacity, the compounds of this invention or compositions containing these compounds, as the active ingredient, are useful in controlling the growth of plants. The plants after treatment exhibit a compact growth habit, reduced water uptake (i.e. water utilization) and darker leaf coloration (increased chlorophyll content per unit area of the leaves).

The compounds can be applied to the plants through the soil, i.e., the compound is taken up by the roots or underground stems, or the compounds can be applied directly to the plant itself, i.e., above ground surfaces of the plant, seeds, roots or tubers and the like.

The exposure of viable plants and plant parts to the action of a growth regulating amount of the compounds of the present invention is essential and critical for the practice of the present invention. The exact dosage to be employed, is not the same for all plants with all compounds and is dependent upon the response desired in the plant as well as such other factors as the plant species and the stage of growth at which treatment is made, the soil type and the depth at which the compounds are distributed in the soil, and climatic conditions such as temperature, wind and especially rainfall.

In foliar treatments for the control and inhibition of plant growth, good results are obtained when from 0.0001 pound to 50 pounds or more, preferably 0.0006 to 24 pounds of the compounds are applied per acre in applications for the control of the growth of germinant seeds, emerging seedlings and established vegetation. Good results are obtained when the compounds are distributed in the soil at the above dosage and through such a cross section of the soil as to provide for the presence therein of an effective concentration of the compounds. In such applications, it is desirable that the compounds be distributed to a depth of at least 0.25 inch. In general, good results are obtained at dosages of from about 0.1 part or more, and preferably from 0.5 to 50 parts or more by weight of active agent per million parts by weight of soil.

The method of the present invention can be practiced by distributing the unmodified compounds in growth media or upon the surfaces of the above-ground portion of plants. However, the present method also embraces the similar employment of liquid or dust compositions containing the compounds. In such usages, the compounds can be modified with one or a plurality of additaments or adjuvants including water or other liquid carriers, surface active dispersing agents, and finely divided solids. Depending upon the concentration of the compounds, such augmented compositions are adapted to be distributed in soil or upon the above ground surfaces of plants, or to be employed as concentrates and subsequently diluted with additional inert carrier to produce the ultimate treating compositions. In compositions where the adjuvant or helper is a finely divided solid, a surface active agent or the combination of a surface active agent and a finely divided solid, and/or a liquid additament, the adjuvant and/or adjuvants cooperate with the compounds so as to facilitate the invention and obtain an improved and outstanding result.

As indicated above, the compound can be directly applied to seeds prior to planting. The application to seeds of an effective growth regulating dosage of the active compounds is essential and critical for the practice of the present invention. Good results are obtained when the seeds are treated with the compounds at a dosage of from about 0.0001 pound per hundred pounds of seed up to the phytotoxic threshold. The latter is about 0.1 pound per hundred pounds of seed inasmuch as lasting phytotoxic effects are obtaining with many plants at dosage levels above the 0.1 pound level. Depending on the particular plant species and variety and on the growing conditions some undesirable phytotoxic effects may be encountered even below the 0.1 pound level. Within the above set forth treating range, the maximum growth response is obtained, and any phytotoxicity experienced in the very early stages of plant growth is usually overcome as the plant begins the growth and maturation habit which is characterized by the present process.

The treatment of the seeds may be accomplished by shaking or otherwise contacting the seeds with a dust composition containing the active agent, or by wetting the seeds with a liquid composition. In a convenient method of application, the compositions are applied in the form of dusts or sprays to the seeds as the latter are transported on the surface of a slowly moving belt or a perforated material such as a wire screen. In still another method, the required dosage of active agent can be applied on and about the seeds by the seed planting implement either in the hopper box or as the seeds are being planted into the soil or other growth media.

The exact concentration of the compounds to be employed in the treating compositions is not critical and may vary considerably provided the required dosage of the compounds is supplied in the growth medium or upon the plant foliage. The concentration of the compound in liquid compositions employed to supply the desired dosage generally is from about 0.001 to 50 percent by weight although concentrations as low as 0.0001 percent and as high as 90 percent by weight are sometimes advantageously employed. In dusts, the concentration of toxicant is from about 0.1 to 90 percent by weight and usually not in excess of about 20 percent. In both liquid and dust compositions to be employed as concentrates, the compounds can be present in a concentration of from 5 to 98 percent by weight.

The quantity of treating compositions to be applied can vary considerably provided that the required dosage of the compound or active ingredient is applied in a sufficient amount of the finished composition to cover adequately the vegetation to be treated or to facilitate the penetration and distribution of said ingredient in growth media. The required amount of the active ingredient in the soil conveniently can be supplied per acre treated in from 1 to 27,000 gallons or more of the liquid carrier or in from 50 to 2,000 pounds of the solid carrier. In the treatment of seedlings good coverage is obtained when using from 10 to 60 gallons of finished spray composition per acre. Where large plants are concerned, it is frequently desirable to employ up to 600 gallons or more of the finished spray composition per acre to assure complete coverage of the above-ground portion of the vegetation. In the application of dusts to plant foliage, good results are obtained with from 40 to 2,000 pounds of finished dust per acre, the only requirement being that the required toxicant dosage be supplied in sufficient dust to achieve good coverage of the foliage.

Liquid compositions containing the desired amount of active ingredient can be prepared by dispersing the compounds in water or in organic liquid, with or without the aid of a suitable surface active dispersing agent such as an ionic or non-ionic emulsifying agent. Suitable organic liquid carriers include the agricultural spray oils and the petroleum distillates such as diesel fuel, kerosene, fuel oil, and naphthas. The organic liquid compositions can contain a small amount of water as a solvent for the active ingredient. In such compositions, the carrier comprises an emulsion, namely, a mixture of water, emulsifying agent and organic liquid. In the liquid compositions, the choice of dispersing and emulsifying agent and the amount thereof employed is dictated by the nature of the composition and by the ability of the agent to facilitate the dispersion of the compounds in the carrier to produce the desired composition or to facilitate the wetting of surfaces upon which the compositions are applied. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps and the like.

In the preparation of dust compositions, the active ingredient is dispersed in and on a finely divided solid such as clay, talc, chalk, gypsum, sugar, salt, bicarbonate, fertilizer and the like. In such operations, the finely divided carrier is mechanically mixed or ground with the compounds. Similarly, dust compositions containing the compounds can be prepared from various of the solid surface active dispersing agents such as bentonite, fuller's earth, attapulgite and other clays. Depending upon the proportion of ingredients, these dust compositions can be employed as concentrates and subsequently diluted with additional solid surface active dispersing agent or with chalk, talc or gypsum, sugar, salt, fertilizer, and the like to obtain the desired amount of active ingredient in a composition adapted to be employed for the modification of the growth of plants. Also such dust compositions can be dispersed in water with or without the aid of a dispersing agent to form spray mixtures.

When operating in accordance with the present invention, growth regulating amounts of the compounds are dispersed in soil or growth media in any convenient fashion. Applications to growth media can be carried out by simply mixing with the media, by applying to the surface of soil and thereafter dragging or discing into the soil to the desired depth or by employing a liquid carrier to accomplish the penetration and impregnation. The application of spray and dust compositions to the surface of soil or to the above-ground surfaces of plants can be carried out by conventional methods, e.g., power dusters, boom and hand sprayers and spray dusters.

In a further method, the distribution of the compounds in soil can be accomplished by introducing the agents in the water employed to irrigate the soil. In such procedures, the amount of water can be varied with the porosity and water-holding capacity of the soil to obtain the desired depth of distribution of the toxicants.

The expression "growth media" is employed in the present specification and claims in its broadest sense to be inclusive of all conventional low clay content, soils and growth media and thus refers to any substance or media in which vegetation may take root and grow, and is intended to include not only earth but compost, manure, muck, humus and sand and the like, adapted to support plant growth.

The expression "surface active dispersing agent" as herein employed is intended to include all agents which are capable of acting at the interfacial surface as the dispersion medium. Thus, the term is inclusive of the solid emulsifying agents such as finely divided aluminum hydroxide and finely divided bentonite, fuller's earth, attapulgite and other clays, as well as the ionic and non-ionic wetting and emulsifying agents such as the alkaline earth metal caseinates, alkyl aryl sulfonates, sulfonated oils, complex organic ester derivatives, complex ether alcohols, and the like.

The finely divided inert solid or carrier as herein described refers to materials which are incapable of facilitating dispersion but which serve as a distribution medium for the active compounds. They include finely divided materials such as chalk, talc, gypsum, sugar, salt, bicarbonate, fertilizers, and so forth.

EXAMPLE VIII

Tests were conducted to determine the effectiveness of triisopentyl-3-(trifluoromethyl)benzyl ammonium chloride in retarding the growth of soybean plants by the treatment of the seeds prior to planting. In this operation, soybean seeds of the variety Corosoy were treated with various dilutions of a solution prepared by dissolving a predetermined amount of the compound, as the sole active ingredient, in a predetermined amount of water containing 0.1% of the surfactant Tween 20.[a] The treatment was carried out by adding 5 milliliters of one of the dilutions to 50 grams of the seed, to give a predetermined dosage rate based on 100 pounds of seeds, and tumbling the seeds until all of the seeds were uniformly coated with the solution. The treated seeds were dried and planted in good loamy soil and maintained under greenhouse conditions for 18 days. At the end of this period, the plants were examined to determine the percentage of growth retardation produced by the compounds as compared with check plants which were grown from seeds treated with water and Tween 20 but no active toxicants. The results of this examination, and the dosage of the compound is set forth below in Table II.

TABLE II

| Compound | Percent Growth Retardation of Soybean Plants at Indicated Treatment Rates per 100 lbs. Seed | | |
|---|---|---|---|
| | 0.1 lb. | 0.01 lb. | 0.001 lb. |
| Triisopentyl-(3-(trifluoromethyl)-benzyl)ammonium chloride | 91 | 83 | 39 |
| Check | 0 | 0 | 0 |

(a) Tween 20 - proprietary material of Imperial Chemical Industries, U.S. which is a polyoxyethylene (20) sorbitan monolaurate.

EXAMPLE IX

Tests were conducted to determine the effectiveness of triisopentyl-3-(trifluoromethyl)benzyl ammonium chloride in retarding the growth of soybean plants by the treatment of the seeds prior to planting. In this operation, soybean seeds of the variety Corosoy were treated with various dilutions of a solution prepared by dissolving a predetermined amount of the compound, as the sole active ingredient, in a predetermined amount of water containing 0.1% of the surfactant Tween 20. The treatment was carried out by adding 5 milliliters of one of the dilutions to 50 grams of the seed, to give a predetermined dosage rate based on 100 pounds of seeds, and tumbling the seeds until all of the seeds were uniformly coated with the solution. The treated seeds were dried and planted in good loamy soil and maintained under greenhouse conditions for 5 weeks. At the end of this period, the plants were examined to determine the percentage of growth retardation produced by the compounds as compared with check plants which were grown from seeds treated with water and Tween 20 but no active toxicants. The results of this examination, and the dosage of the compound is set forth below in Table III.

TABLE III

Percent Growth Retardation of Soybean Plants at Indicated Treatment Rates in Pound of Active Material per 100 lbs. Seed

| Compound | 0.02 | 0.01 | 0.005 | 0.0012[a] | 0.0007[a] |
|---|---|---|---|---|---|
| Tri-n-butyl-(3-(trifluoromethyl)-benzyl)ammonium chloride | 73 | 58 | 37 | 10 | 5 |
| Check | 0 | 0 | 0 | 0 | 0 |

[a]Calculated by Probit analysis.

EXAMPLE X

Varous dilutions of an aqueous solution of triisopentyl-3-(trifluoromethyl)benzylammonium chloride prepared as in Example VIII, were sprayed onto the foliage of soybean plants variety Chippewa 64 at the rate of 25 gallons per acre resulting in an application rate equal to a predetermined gram per acre rate. The soybean seedlings were raised under greenhouse conditions in 2½×2½×3 inch plant bands employing "Jiffy Mix" a conventional commercial potting media. The plants were treated when 12–14 days old and before there was expansion of the first trifoliate leaf. The plant bands containing the treated plants were placed on a one-half inch layer of the potting media in the bottom of 8×8 inch plastic trays and the trays were maintained under greenhouse conditions for growth and observation. In addition, untreated plants were prepared and maintained as controls. The plants were watered as needed. There were ten replications for each treatment.

Two weeks after treatment, new stem growth was estimated by measuring stem length from the node of the primary leaves to the apex. Growth of the plants at the various levels of treatment was calculated as a percentage of control plant growth and the results plotted on log-probability paper. The quantity of the test compound (on a gram per acre basis) required to give a 50 percent control of plant growth was thereafter estimated from the best straight line drawn through the plotted data points. It was found that only 9 grams per acre of this test compound was necessary to give a 50 percent retardation ($GI_{50}$) of the growth of the soybean plants. The control plants were found to be healthy but not quite as dark green as the treated plants.

EXAMPLE XI

Aqueous spray compositions were prepared containing a predetermined amount of tri-n-butyl-3-(trifluoromethyl)benzyl)ammonium chloride, as the sole active agent, dissolved in a predetermined amount of a water-surfactant mixture.

Various species of trees of about two years age and two to four feet height were sprayed to run-off with varying concentrations of the above test dispersion. At the same time, additional trees were sprayed with a water-surfactant mixture containing no active agent to serve as controls. After treatment, the trees were maintained under normal field conditions for 3 months. At the end of this period, the trees were evaluated to determine the percent growth retardation at the various treating dilutions. The results of this evaluation, the variety of the trees and the amount of the compound employed is set forth below in Table IV.

TABLE IV

Percent Growth Retardation of Various Tree Species at the Indicated Dosage Rate based on Pound per 100 Gallons of Ultimate Treating Composition

| Tree Specie | 1 | 2 | 3 | 0 |
|---|---|---|---|---|
| Silver Maple | 11 | 66 | 73 | 0 |
| Eucalyptus | 37 | 15 | 18 | 0 |
| Black Oak | 23 | 0 | 28 | 0 |
| Arizona Cypress | −35[a] | 23 | 15 | 0 |
| Sweet Gum | 85 | 73 | 80 | 0 |

[a]Some stimulation noted, appears to be species specific phenomenon whereby at a very low dosage rate, the compound acted as a growth stimulant. Such phenomenon is not unusual for growth stunters.

EXAMPLE XII

An aqueous spray composition was prepared by dissolving a predetermined amount of triisopentyl-3-(trifluoromethyl)benzyl)ammonium chloride in a predetermined amount of a water-surfactant mixture to give an aqueous dispersion containing 2,400 parts of the compound per million parts of the ultimate dispersion.

Silver maple trees of like age were grown to a height of 12 to 18 inches under greenhouse conditions in good, loamy soil. The trees were sprayed to run-off with one of the spray compositions. Additional trees were sprayed with only a water-surfactant mixture to serve as controls. The trees were thereafter maintained under greenhouse conditions for 28 days. At the end of this period, it was found that the silver maple trees had a retardation in growth over the control trees of 17 percent and were very healthy.

EXAMPLE XIII

Test solutions were prepared by admixing a predetermined amount of tri-n-butyl-3-(trifluoromethyl)benzyl)ammonium chloride with a predetermined amount of a water-surfactant mixture to obtain aqueous dispersion containing the equivalent of 900, 1800 and 3600 (PPM) parts of the compound per million parts of the ultimate dispersion (this is also equivalent to 0.75, 1.5 and 3 pounds of the test compound per 100 gallons of the ultimate dispersion).

Rubber tree seedlings of the species Hevea brasiliensis grown to a height of 15–20 centimeters were sprayed to the point of run-off with one of the above dispersions (8 replications with 9 seedlings per replication). At the same time, additional trees were treated with only water and surfactant to serve as controls. After treatment, the trees were maintained under conditions conducive for good plant growth for one month. At the end of this time period, the plants were examined to determine the growth retarding effects obtained from the treatment with the above compound. The results of this examination, the average growth of the trees and the percent retardation is set forth below in Table V.

TABLE V

| Test Compound | Dosage rate in PPM | Average growth of rubber trees in Centimeters | Percent retardation of tree growth |
|---|---|---|---|
| Tri-n-butyl-(3-(tri-fluoromethyl)benzyl)-ammonium chloride | 3600 | 5.8 | 53 |
| | 1800 | 11.9 | 4 |
| | 900 | 12.6 | 0[a] |

TABLE V-continued

| Test Compound | Dosage rate in PPM | Average growth of rubber trees in Centimeters | Percent retardation of tree growth |
|---|---|---|---|
| Control | — | 12.3 | — |

(a)actual 2 percent increase in growth over control

EXAMPLE XIV

An aqueous spray composition was prepared by dissolving a predetermined amount of one of the hereinafter set forth active compounds in a predetermined amount of a water-surfactant mixture to give aqueous dispersions containing varying amounts of the active compound.

Silver maple trees of like age were grown to a height of 12 to 18 inches under greenhouse conditions in good loamy soil. The trees were sprayed with one of the spray compositions at a dosage rate equivalent to from 0.56 to 2.24 pounds of the active compound per 100 gallons of the ultimate dispersion. Additional trees were sprayed with only a water-surfactant mixture to serve as controls. The trees were thereafter maintained under greenhouse conditions for 28 days. At the end of this period, the trees were evaluated to determine the degree of growth retardation of the terminal growth of the trees which occurred from the treatment. The results of this examination, the compounds employed and the percent growth retardation is set forth below in Table VI.

TABLE VI

| Compound No. | Rate of Application in Pounds Per 100 Gallons of Ultimate Dispersion | Terminal Growth of Silver Maple Trees in Centimeters (cm) | Percent Retardation in Terminal Growth |
|---|---|---|---|
| 1 | 2.24 | 19.8 | 64 |
|   | 1.12 | 41.4 | 24 |
|   | 0.56 | 30.4 | 44 |
| 2 | 2.24 | 13.6 | 75 |
|   | 1.12 | 14.5 | 74 |
|   | 0.56 | 26.5 | 52 |
| 3 | 2.24 | 45.0 | 18 |
|   | 1.12 | 41.5 | 24 |
|   | 0.56 | 46.0 | 16 |
| 4 | 2.24 | 13.1 | 76 |
|   | 1.12 | 12.8 | 77 |
|   | 0.56 | 34.9 | 36 |
| 25 | 2.24 | 37.8 | 31 |
|   | 1.12 | 24.9 | 55 |
|   | 0.56 | 32.8 | 40 |

<sup>a</sup>For compound Number 1, terminal growth for control plants was 54.3 centimeters For compound Numbered 2, 3, 4 and 25, terminal growth for control was 54.9 centimeters.

EXAMPLE XV

An aqueous spray composition was prepared by dissolving a predetermined amount of one of the hereinafter set forth active compounds in a predetermined amount of a water-surfactant mixture to give aqueous dispersions containing varying amounts of the active compound.

Silver maple trees of like age were grown to a height of 12 to 18 inches under greenhouse conditions in good loamy soil. The trees were sprayed to run-off with one of the spray compositions at a dosage rate equivalent to from 0.75 to 3.0 pounds of the active compound per 100 gallons of the ultimate dispersion. Additional trees were sprayed with only a water-surfactant mixture to serve as controls. The trees were thereafter maintained under greenhouse conditions for 28 days. At the end of this period, the trees were evaluated to determine the degree of growth retardation of the terminal growth of the trees which occurred from the treatment. The results of this examination, the compounds employed and the percent growth retardation is set forth below in Table VII.

TABLE VII

| Compound No. | Rate of Application in Pounds Per 100 Gallons of Ultimate Dispersion | Terminal Growth of Silver Maple Trees in Centimeters (cm) | Percent Retardation in Terminal Growth |
|---|---|---|---|
| 5 | 3.0 | 7.1 | 80 |
|   | 1.5 | 5.8 | 84 |
|   | 0.75 | 9.5 | 73 |
| 6 | 3.0 | 30.0 | 32 |
|   | 1.5 | 31.8 | 28 |
|   | 0.75 | 43.0 | 3 |
| 11 | 3.0 | 20.5 | 27 |
|   | 1.5 | 13.0 | 54 |
|   | 0.75 | 24.7 | 12 |
| 12 | 3.0 | 12.8 | 54 |
|   | 1.5 | 17.5 | 38 |
|   | 0.75 | 27.3 | 3 |
| 13 | 3.0 | 23.0 | 17 |
|   | 1.5 | 27.0 | 2 |
|   | 0.75 | 30.0 | −8 |
| 15 | 3.0 | 19.5 | 30 |
|   | 1.5 | 22.8 | 18 |
|   | 0.75 | 18.3 | 34 |
| 16 | 3.0 | 20.5 | 43 |
|   | 1.5 | 31.0 | 13 |
|   | 0.75 | 32.5 | 7 |
| 17 | 3.0 | 13.2 | 46 |
|   | 1.5 | 18 | 27 |
|   | 0.75 | 19.7 | 20 |
| 7 | 3.0 | 5.0 | 82 |
|   | 1.5 | 12.0 | 56 |
|   | 0.75 | 13.5 | 50 |
| 9 | 3.0 | 8.3 | 83 |
|   | 1.5 | 14.0 | 70 |
|   | 0.75 | 15.8 | 66 |
| 8 | 3.0 | 5.8 | 88 |
|   | 1.5 | 15.5 | 66 |
|   | 0.75 | 15.3 | 68 |
| 20 | 3.0 | 17.7 | 60 |
|   | 1.5 | 8.6 | 80 |
|   | 0.75 | 23.2 | 47 |
| 21 | 3.0 | 14.3 | 68 |
|   | 1.5 | 12.5 | 72 |
|   | 0.75 | 34 | 23 |
| 26 | 3.0 | 7.8 | 84 |
|   | 1.5 | 13.0 | 72 |
|   | 0.75 | 15.8 | 66 |
| Control | — | (a) | — |

(a) Stimulation noted, appears to be phenomenon whereby at a low dosage rate, the compound acted as a growth stimulant. Action not unusual for growth stunter.
(b) For compound Number 5, terminated growth of control plants was 35.0 centimeters. For compounds numbered 6, 20 and 21, terminal growth of control plants was 44.2 centimeters. For compounds numbered 11 and 12, terminal growth of control plants was 28.0 centimeters. For compounds numbered 13 and 15, terminal growth of control plants was 27.8 centimeters. For compound number 16, terminal growth of control plants was 35.7 centimeters. For compound number 17, terminal growth of control plants was 24.6 centimeters. For compound number 7, terminal growth of control plants was 27.1 centimeters. For compounds numbered 8, 9 and 26, terminal growth of control plants was 47.5 centimeters.

EXAMPLE XVI

Tests were conducted to determine the effectiveness of tri-n-butyl-(3-trifluoromethyl)benzyl)ammonium chloride in reducing the water uptake of coffeeweed plants.

A series of 4 ounce wide mouth jars were each filled with 120 g of air dried Knightsen sand (94.3% sand, 1.3% silt and 4.4% clay which contains 0.08% organic carbon). Thirty ml of water containing a predetermined amount of above set forth compound dissolved therein was added to each jar to give dosage rates of from 0 to 20 ppm of the compound. The jars were seeded with about 20 seeds of coffeeweed (*Daubentonia texana* Pierce) and placed in a growth chamber (16 hour day, 80° F. day temperature, 65° F. night temperature) with constant 70% humidity. Two weeks after seeding, the plants were removed from the sand with gentle water washing. The roots were then washed in ½ strength Hoagland solution (a complete nutrient solution) to remove all of the adhering sand.

The plants were then placed with their roots in a 15 ml tube filled with 14 ml of a dilute complete nutrient solution (Hoaglands solution). The plants were held in place in the tubes with a soft polyurethane plug which had been split half way through. The tubes were supported in a sand box and placed in a greenhouse on a cloudy-bright day.

After 45 hours, the amount of nutrient uptake for each dosage rate was measured by comparing the volume of initial solution with the volume of solution remaining after 45 hours. The concentration of the test compound, the height of the plants and the nutrient uptake are set forth below in Table VIII.

TABLE VIII

| Concentration of tri-n-butyl-(3-(trifluoro-methyl)benzyl)-ammonium chloride in ppm water | Plant Height in Centimeters (cm) after two weeks of growth | Nutrient uptake in ml after 45 hours | Percent reduction in use of nutrient solution as a percent of control |
|---|---|---|---|
| 0 | 6.35 | 5.49 | — |
| 0.625[a] | 7.37 | 5.76 | +4.9 |
| 1.250 | 6.98 | 3.90 | 28 |
| 2.500 | 4.09 | 4.10 | 25 |
| 5.000 | 3.38 | 4.72 | 14 |
| 10.000 | 2.00 | 3.60 | 34 |
| 20.000 | 1.20 | 3.58 | 35 |

[a]Slight stimulation of plant growth at this dosage rate with slight increase in water uptake. At higher dosage rates, the effect is reversed.

EXAMPLE XVII

Tests were conducted to determine the effectiveness of tri-n-butyl-(3-trifluoromethyl)benzyl)ammonium chloride in reducing the water uptake of soybeans.

Soybean plants of the variety corosoy were grown in a greenhouse in pots containing a sandy soil. Various dilutions of an aqueous solution of tri-n-butyl-(3-trifluoromethyl)benzyl)ammonium chloride prepared by dissolving a predetermined amount of the compound in a predetermined amount of water containing 0.1% of a wetting agent. The plants were sprayed to run-off with the above solutions at the time of the expansion of the first trifoliate leaf (~12-14 days old). Two weeks later, the plants were measured and then the soil washed away from the roots with gentle water pressure. The roots were washed with dilute Hoaglands solution to remove all the adhering sand. The plants were then placed with their roots in a 125 ml Ehrlenmeyer flask containing 100 ml of dilute Hoaglands solution. The flasks were wrapped and sealed with aluminum foil and then placed in a greenhouse. Seventy-two hours later, the amount of nutrient uptake at each dosage rate was measured by comparing the volume of initial solution with the volume of solution remaining after 72 hours. The concentration of the test compound, the amount of growth for the plants and the nutrient uptake are set forth below in Table IX.

TABLE IX

| Concentration of tri-n-butyl-(3-(trifluoro-methyl)benzyl)-ammonium chloride in ppm | Plant growth in centimeters(cm) two weeks after treatment | Nutrient uptake in ml after 72 hours | Percent reduction in use of nutrient solution as a percent of control |
|---|---|---|---|
| 0.00 | 13.4 | 63.8 | — |
| 0.47 | 12.1 | 47.2 | 26 |
| 0.94 | 10.7 | 55.6 | 13 |
| 1.90 | 10.0 | 48.8 | 23 |
| 3.80 | 8.6 | 59.6 | 7 |

EXAMPLE XVIII

Tests were conducted to determine the effectiveness of tri-n-butyl-(3-(trifluoromethyl)benzyl)ammonium chloride in reducing the water uptake of peanuts and in finding the optimum chemical concentration to achieve this result.

Peanuts (*Arachis hypogea*) grown in a greenhouse in pots containing a sandy soil. When the peanuts were 8 days old, they were sprayed to the point of run-off with various dilutions of aqueous solutions of tri-n-butyl-(3-trifluoromethyl)benzyl)ammonium chloride. These solutions were prepared by dissolving a predetermined amount of the compound in a predetermined amount of water containing 0.1% of a wetting agent. Three weeks after treatment, the plants were removed from the sand they were growing in and the sand gently washed from the roots. The roots were then washed with dilute Hoaglands solution to remove any adhering sand. The plants were then placed with their roots in a 125 ml Ehrlenmeyer flask containing 100 ml of dilute Hoaglands solution. The flasks were wrapped and sealed with aluminum foil and then placed in a greenhouse. Forty-eight hours later, the amount of nutrient uptake for each dosage rate was measured by comparing the volume of initial solution with the volume of solution remaining after 48 hours. The tops of the plants were cut off and then cut into 2–3 centimeter segments and dried in an oven at 95° C. for 24 hours. The weights of the tops, the concentration of the test compound, the nutrient uptake and the ratio of the uptake to the dry weight of the plant tops (i.e. number of ml of nutrient taken up per gram of dry weight of the plant tops) are set forth below in Table X.

TABLE X

| Concentration of tri-n-butyl-(3-(trifluoro-methyl)benzyl)-ammonium chloride in ppm of water | Dry weight of peanut tops in gms per plant | Nutrient uptake in ml after 48 hours | Number of ml of nutrient uptake per gram of dried tops |
|---|---|---|---|
| 0 | 2.42 | 41.5 | 17.1 |
| 0.23 | 2.35 | 35.5 | 15.1 |
| 0.90 | 3.06 | 40.8 | 13.3[a] |
| 3.70 | 2.94 | 45.7 | 15.5 |
| 15.00 | 2.58 | 49.0 | 19.0 |
| 60.00 | 2.46 | 40.0 | 16.3 |
| 240.00 | 2.19 | 41.3 | 18.9 |

[a]Optimum dosage to give greatest water use efficiency.

EXAMPLE XIX

Tests were conducted to determine the effectiveness of tri-n-butyl-(3-(trifluoromethyl)benzyl)ammonium chloride in reducing the water uptake of sugar beets and in finding the optimum chemical concentration to achieve this result.

Sugar beets grown in a greenhouse in pots containing a sandy soil. When the plants were 8 days old, they were sprayed to the point of run-off with various dilutions of aqueous solutions of tri-n-butyl-(3-(trifluoromethyl)benzyl)ammonium chloride. These solutions were prepared by dissolving a predetermined amount of the compound in a predetermined amount of water containing 0.1% of a wetting agent. Three weeks after treatment, the plants were removed from the sand they were growing in and the sand gently washed from the roots. The roots were then washed with dilute Hoaglands solution to remove any adhering sand. The plants were then placed with their roots in a 125 ml Ehrlenmeyer flask containing 100 ml of dilute Hoaglands solution. The flasks were wrapped and sealed with aluminum foil and then placed in a greenhouse. Forty-four hours later, the amount of nutrient uptake for each dosage rate was measured by comparing the volume of initial solution with the volume of solution remaining after 44 hours. The tops of the plants were cut off and the weights of the tops, the concentration of the test compound, the nutrient uptake and the ratio of the uptake to the weight of the plant tops (i.e. number of ml of nutrient taken up per gram of plant tops) are set forth below in Table XI.

TABLE XI

| Concentration of tri-n-butyl-(3-(trifluoromethyl)benzyl)-ammonium chloride in ppm | Fresh weight of sugar beet tops in gms per plant | Nutrient uptake in ml after 44 hours | Number of ml of nutrient uptake per gram of tops |
|---|---|---|---|
| 0.0 | 19.9 | 48.4 | 2.43 |
| 0.1 | 22.1 | 59.1 | 2.67 |
| 1.0 | 26.7 | 52.9 | 1.98[a] |
| 10.0 | 25.8 | 71.9 | 2.79 |
| 100.0 | 19.6 | 63.0 | 3.22 |

[a]Optimum dosage to give greatest water use efficiency.

What is claimed is:

1. A compound corresponding to the formula

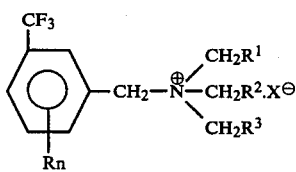

wherein R represents hydrogen, chloro, bromo or trifluoromethyl; n represents an integer of from 1 or 2, with the proviso that when R is trifluoromethyl, n is 1; $R^1$, $R^2$ and $R^3$ each independently represent ethyl, n-propyl, n-butyl, isobutyl, ethynyl, vinyl or ethoxymethyl and X represents a non-phytotoxic anion.

2. A compound as defined in claim 1 wherein R is hydrogen.

3. A compound as defined in claim 1 wherein R is chloro or bromo and n is 1.

4. A compound as defined in claim 1 wherein R is chloro or bromo and n is 2.

5. A compound as defined in claim 1 wherein each of $R^1$, $R^2$ and $R^3$ are each n-propyl.

6. A compound as defined in claim 1 wherein at least one of $R^1$, $R^2$ and $R^3$ is ethynyl or vinyl and the other two of $R^1$, $R^2$ and $R^3$ are selected from the group consisting of ethyl, n-propyl, n-butyl and isobutyl.

7. A compound as defined in claim 1 wherein R is hydrogen and $R^1$, $R^2$ and $R^3$ are each selected from the group consisting of ethyl, n-propyl, n-butyl and isobutyl.

8. The compound as defined in claim 7 which is tri-n-butyl(3-(trifluoromethyl)benzyl)ammonium chloride.

9. The compound as defined in claim 3 which is tri-n-butyl(2-chloro-5-(trifluoromethyl)benzyl)ammonium chloride.

10. A composition useful for treating plants to obtain a reduction of the linear growth of said plants which consist essentially of an effective plant growth regulating amount of a compound corresponding to the formula

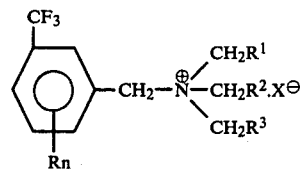

wherein R represents hydrogen, chloro, bromo or trifluoromethyl; n represents an integer of from 1 or 2, with the proviso that when R is trifluoromethyl, n is 1; $R^1$, $R^2$ and $R^3$ each independently represent ethyl, n-propyl, n-butyl, isobutyl, ethynyl, vinyl or ethoxymethyl and X represents a non-phytotoxic anion, in admixture with an inert carrier therefor.

11. A composition as defined in claim 10 wherein R is hydrogen.

12. A composition as defined in claim 10 wherein R is chloro or bromo and n is 1.

13. A composition as defined in claim 10 wherein R is chloro or bromo and n is 2.

14. A composition as defined in claim 10 wherein each of $R^1$, $R^2$ and $R^3$ are each n-propyl.

15. A composition as defined in claim 10 wherein at least one of $R^1$, $R^2$ and $R^3$ is ethynyl or vinyl and the other two of $R^1$, $R^2$ and $R^3$ are selected from the group consisting of ethyl, n-propyl, n-butyl and isobutyl.

16. A composition as defined in claim 10 wherein R is hydrogen and $R^1$, $R^2$ and $R^3$ are each selected from the group consisting of ethyl, n-propyl, n-butyl and isobutyl.

17. The composition as defined in claim 16 wherein the active material is tri-n-butyl(3-trifluoromethyl)benzyl)ammonium chloride.

18. The composition as defined in claim 12 wherein the active material is tri-n-butyl(2-chloro-5-(trifluoromethyl)benzyl)ammonium chloride.

19. The composition as defined in claim 1 in which the active material is present in the amount of from 0.0001 to 90 percent by weight of the ultimate composition.

20. A method for regulating the growth of plants to obtain a reduction of the linear growth of said plants which comprises contacting plants, plant parts or their habitat with a growth regulating amount of a composition which consist essentially of a compound corresponding to the formula

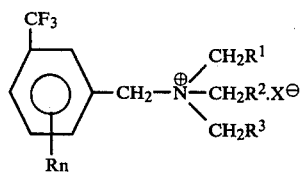

wherein R represents hydrogen, chloro, bromo or trifluoromethyl; n represents an integer of from 1 or 2, with the proviso that when R is trifluoromethyl, n is 1; $R^1$, $R^2$ and $R^3$ each independently represent ethyl, n-propyl, n-butyl, isobutyl, ethynyl, vinyl or ethoxymethyl and X represents a non-phytotoxic anion, in admixture with an inert carrier therefor.

21. The method as defined in claim 20 wherein R is hydrogen.

22. The method as defined in claim 20 wherein R is chloro or bromo and n is 1.

23. The method as defined in claim 20 wherein R is chloro or bromo and n is 2.

24. The method as defined in claim 20 wherein each of $R^1$, $R^2$ and $R^3$ are each n-propyl.

25. The method as defined in claim 20 wherein at least one of $R^1$, $R^2$ and $R^3$ is ethynyl or vinyl and the other two of $R^1$, $R^2$ and $R^3$ are selected from the group consisting of ethyl, n-propyl, n-butyl and isobutyl.

26. The method as defined in claim 20 wherein R is hydrogen and $R^1$, $R^2$ and $R^3$ are each selected from the group consisting of ethyl, n-propyl, n-butyl and isobutyl.

27. The method as defined in claim 26 wherein the active material is tri-n-butyl(3-trifluoromethyl)benzyl)ammonium chloride.

28. The method as defined in claim 22 wherein the active material is tri-n-butyl(2-chloro-5-(trifluoromethyl)benzyl)ammonium chloride.

29. The method as defined in claim 20 in which plant seeds are contacted.

30. The method as defined in claim 20 in which the above-ground portions of the plants are contacted.

31. The method as defined in claim 20 in which the habitat is soil and said soil is contacted.

32. The method as defined in claim 29 wherein the seeds are contacted with from 0.0001 to 0.1 pound of the active material per 100 pounds of seed.

33. The method as defined in claim 30 wherein the above-ground portions of the plants are contacted with from 0.0001 pound to 50 pounds of the active material per acre.

34. A method for reducing the water uptake requirement of plants which comprises contacting plants, plant parts or their habitat with an amount of a composition effective to reduce the water uptake of said plants, said composition consisting essentially of, a compound corresponding to the formula

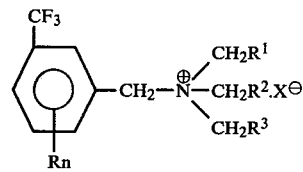

wherein R represents hydrogen, chloro, bromo or trifluoromethyl; n represents an integer of from 1 or 2, with the proviso that when R is trifluoromethyl, n is 1; $R^1$, $R^2$ and $R^3$ each independently represent ethyl, n-propyl, n-butyl, isobutyl, ethynyl, vinyl or ethoxymethyl and X represents a non-phytotoxic anion, in admixture with an inert carrier therefor.

35. The method as defined in claim 34 wherein R is hydrogen.

36. The method as defined in claim 34 wherein R is chloro or bromo and n is 1.

37. The method as defined in claim 34 wherein R is chloro or bromo and n is 2.

38. The method as defined in claim 34 wherein each of $R^1$, $R^2$ and $R^3$ are each n-propyl.

39. The method as defined in claim 34 wherein at least one of $R^1$, $R^2$ and $R^3$ is ethynyl or vinyl and the other two of $R^1$, $R^2$ and $R^3$ are selected from the group consisting of ethyl, n-propyl, n-butyl and isobutyl.

40. The method as defined in claim 34 wherein R is hydrogen and $R^1$, $R^2$ and $R^3$ are each selected from the group consisting of ethyl, n-propyl, n-butyl and isobutyl.

41. The method as defined in claim 40 wherein the active material is tri-n-butyl(3-trifluoromethyl)benzyl)ammonium chloride.

42. The method as defined in claim 34 in which plant seeds are contacted.

43. The method as defined in claim 34 in which the above-ground portions of the plants are contacted.

44. The method as defined in claim 34 in which the habitat is soil and said soil is contacted.

45. The method as defined in claim 42 wherein the seeds are contacted with from 0.0001 to 0.1 pound of the active material per 100 pounds of seeds.

46. The method as defined in claim 43 wherein the above-ground portions of the plants are contacted with from 0.0001 pound to 50 pounds of the active material per acre.

* * * * *